United States Patent
Paret et al.

(10) Patent No.: US 11,666,881 B2
(45) Date of Patent: Jun. 6, 2023

(54) PROCESS FOR PREPARING POLYSUCCINIMIDE DERIVATIVES-BASED MICROCAPSULES

(71) Applicant: Firmenich SA, Satigny (CH)

(72) Inventors: Nicolas Paret, Satigny (CH); Damien Berthier, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/051,909

(22) PCT Filed: Sep. 18, 2019

(86) PCT No.: PCT/EP2019/074949
§ 371 (c)(1),
(2) Date: Oct. 30, 2020

(87) PCT Pub. No.: WO2020/058305
PCT Pub. Date: Mar. 26, 2020

(65) Prior Publication Data
US 2021/0316266 A1    Oct. 14, 2021

(30) Foreign Application Priority Data
Sep. 19, 2018  (EP) .................... 18195506

(51) Int. Cl.
| | | |
|---|---|---|
| B01J 13/16 | (2006.01) | |
| A61K 8/11 | (2006.01) | |
| A61K 8/91 | (2006.01) | |
| A61Q 5/02 | (2006.01) | |
| A61Q 5/12 | (2006.01) | |
| C08G 18/60 | (2006.01) | |
| C11D 3/37 | (2006.01) | |
| C11D 3/50 | (2006.01) | |
| C11D 11/00 | (2006.01) | |

(52) U.S. Cl.
CPC ................ *B01J 13/16* (2013.01); *A61K 8/11* (2013.01); *A61K 8/91* (2013.01); *A61Q 5/02* (2013.01); *A61Q 5/12* (2013.01); *C08G 18/603* (2013.01); *C11D 3/3788* (2013.01); *C11D 3/505* (2013.01); *C11D 11/0017* (2013.01); *A61K 2800/624* (2013.01); *A61K 2800/654* (2013.01)

(58) Field of Classification Search
CPC ... C11D 3/505; C11D 3/3788; C11D 11/0017; C11D 3/3719; C11D 17/0039; A61Q 5/02; A61Q 5/12; B01J 13/16; B01J 13/206; B01J 13/14; A61K 8/11; A61K 8/91; A61K 2800/654; A61K 2800/624; C08G 18/603
See application file for complete search history.

(56) References Cited

U.S. PATENT DOCUMENTS

| | | | | |
|---|---|---|---|---|
| 2002/0048559 A1* | 4/2002 | Shinoda | ................ | C08G 73/16 424/78.36 |
| 2004/0049055 A1* | 3/2004 | Rissanen | ............ | C07D 207/412 548/520 |
| 2007/0010652 A1* | 1/2007 | Angot | .................... | C08G 69/48 528/328 |
| 2014/0271751 A1* | 9/2014 | Schmidt | .................. | B01J 13/14 424/59 |
| 2016/0303006 A1* | 10/2016 | Popplewell | ............ | A61K 8/463 |

FOREIGN PATENT DOCUMENTS

| | | |
|---|---|---|
| CN | 102115570 B | 1/2012 |
| WO | 2010134044 A2 | 11/2010 |
| WO | 2011046561 A1 | 4/2011 |
| WO | 2016131694 A1 | 8/2016 |

OTHER PUBLICATIONS

Tomita et al. Journal of Polymer Science: Part A: Polymer Chemistry, vol. 47, 762-770 (2009). (Year: 2009).*
International Search Report and Written Opinion for corresponding PCT/EP2019/074949 dated Nov. 30, 2019, 12 pages.

* cited by examiner

*Primary Examiner* — Doan T Phan
(74) *Attorney, Agent, or Firm* — Armstrong Teasdale LLP

(57) ABSTRACT

Described herein is a new process for the preparation of polysuccinimide derivatives-based core-shell microcapsules. Also described are microcapsules, as well as perfuming compositions and consumer products including these microcapsules, in particular perfumed consumer products in the form of home care or personal care products.

12 Claims, 1 Drawing Sheet

PROCESS FOR PREPARING POLYSUCCINIMIDE DERIVATIVES-BASED MICROCAPSULES

CROSS-REFERENCE TO RELATED APPLICATIONS

This application is a U.S. National Phase Application of International Patent Application No. PCT/EP2019/074949, filed Sep. 18, 2019, which claims the benefit of priority to European Patent Application No. 18195506.3, filed Sep. 19, 2018, the entire contents of each of which are hereby incorporated by reference herein.

TECHNICAL FIELD

The present invention relates to a new process for the preparation of polysuccinimide derivatives-based core-shell microcapsules. Microcapsules are also an object of the invention. Perfuming compositions and consumer products comprising said microcapsules, in particular perfumed consumer products in the form of home care or personal care products, are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume are needed to protect and later release the core payload when triggered. A key requirement from the industry regarding these systems is to survive suspension in challenging bases without physically dissociating or degrading. This is referred to as stability for the delivery system. For instance, fragranced personal and household cleansers containing high levels of aggressive surfactant detergents are very challenging for the stability of microcapsules.

Polyurea and polyurethane-based microcapsule slurry are widely used for example in perfumery industry for instance as they provide a long lasting pleasant olfactory effect after their applications on different substrates. Those microcapsules have been widely disclosed in the prior art (see for example WO2007/004166 or EP 2300146 from the Applicant).

Therefore, there is still a need to provide new microcapsules, while not compromising on the performance of the microcapsules, in particular in terms of stability in a challenging medium such as a consumer product base, as well as in delivering a good performance in terms of deposition or active ingredient delivery, e.g. olfactive performance in the case of perfuming ingredients.

The present invention is proposing a solution to the above-mentioned problem, based on a new process for the preparation of microcapsules in which a polysuccinimide derivative reacts with a polyfunctional monomer during the interfacial polymerization.

SUMMARY OF THE INVENTION

It has now been surprisingly found, that performing core-shell microcapsules encapsulating hydrophobic material, preferably active ingredients could be obtained by reacting a polyfunctional monomer with a polysuccinimide derivative during the interfacial polymerization. The process of the invention therefore provides a solution to the above-mentioned problems as it allows preparing microcapsules with good performance, notably in terms of deposition.

In a first aspect, the present invention relates to a process for preparing a core-shell microcapsule slurry comprising the following steps:
a) dissolving at least one polyfunctional monomer, in a hydrophobic material, preferably a perfume to form an oil phase;
b) dispersing the oil phase obtained in step a) into an aqueous solution comprising a polysuccinimide derivative to form an oil-in-water emulsion; and
c) performing a curing step to form core-shell microcapsules in the form of a slurry.

In a second aspect, the invention relates to a core-shell microcapsule slurry obtainable by the process as defined above.

A third aspect of the invention is a core-shell microcapsule comprising:
an oil based core comprising a hydrophobic material, and
a shell formed from the reaction between a polyfunctional monomer and a polysuccinimide derivative.

A perfuming composition comprising
(i) microcapsules as defined above, wherein the oil comprises a perfume;
(ii) at least one ingredient selected from the group consisting of a perfumery carrier and a perfumery co-ingredient; and
(iii) optionally at least one perfumery adjuvant is another object of this invention.

Consumer products comprising:
an active base; and
microcapsules or a perfuming composition as defined above, wherein the consumer product are in the form of a personal care composition or a home care composition respectively, are also part of the invention.

DETAILED DESCRIPTION OF THE INVENTION

Figure 1:
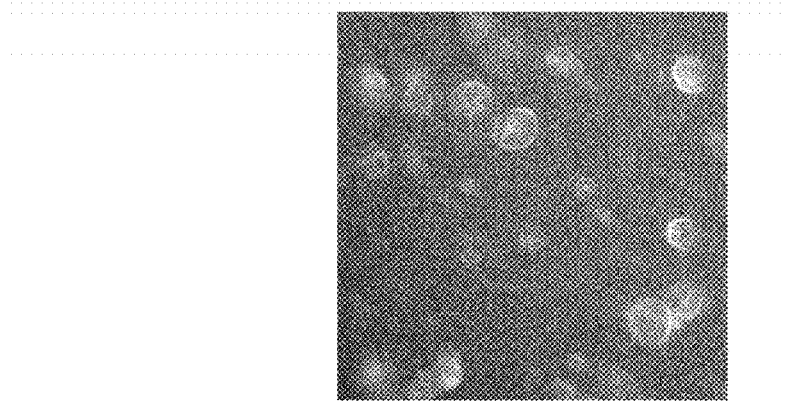
FIG. 1 represents optical microscope observations with UV filter of Capsule H.

Unless stated otherwise, percentages (%) are meant to designate a percentage by weight of a composition.

By "polyfunctional monomer", it is meant a molecule that, as unit, reacts or binds chemically to form a polymer or supramolecular polymer. The polyfunctional monomer of the invention has at least two functions capable of forming a microcapsule shell.

By "polysuccinimide derivative", it is meant a derivative of a polycondensate of aspartic acid.

Preferably, the polysuccinimide derivative is obtained by grafting at least one amine to at least one succinimide repeating unit followed by an optional hydrolysis.

The "succinimide repeating unit" is represented by the unit in brackets in the formula below:

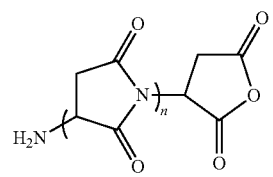

The substitution degree of the polysuccinimide derivative preferably ranges from 5 to 95 mol %, more preferably from 5 to 60 mol %, even more preferably between 5 to 40 mol %.

According to the invention, the terms "amine" or "amine compound" are used indifferently.

By "Hydrophobic material", it is meant a material which forms a two-phase dispersion when mixed with water. According to the invention, the hydrophobic material can be "inert" material like solvents or active ingredients.

By "active ingredient", it is meant a single compound or a combination of ingredients. By "perfume or flavour oil", it is meant a single perfuming or flavouring compound or a mixture of several perfuming or flavouring compounds.

By "consumer product" or "end-product" it is meant a manufactured product ready to be distributed, sold and used by a consumer.

For the sake of clarity, by the expression "dispersion" in the present invention it is meant a system in which particles are dispersed in a continuous phase of a different composition and it specifically includes a suspension or an emulsion.

It has been found that core-shell microcapsules with overall good performance namely a good deposition of the active ingredient on different surfaces could be obtained when the polyfunctional monomer reacts with a polysuccinimide derivative during the interfacial polymerization.

Process for Preparing a Microcapsule Slurry

The present invention therefore relates in a first aspect to a process for preparing a core-shell microcapsule slurry, said process comprising the steps of:
a) dissolving at least one polyfunctional monomer, in a hydrophobic material, preferably a perfume to form an oil phase;
b) dispersing the oil phase obtained in step a) into an aqueous solution comprising a polysuccinimide derivative to form an oil-in-water emulsion; and
c) performing a curing step to form core-shell microcapsules in the form of a slurry.

In one step of the process, an oil phase is formed by admixing at least one hydrophobic material with at least one polyfunctional monomer.

Polyfunctional monomer: According to an embodiment, the polyfunctional monomer is chosen in the group consisting of at least one polyisocyanate, polyanhydride such as poly maleic anhydride; poly acyl chloride; polyepoxide; acrylate monomers such as polyacrylate monomers, polymethacrylate; polyalkoxysilane, and mixtures thereof.

Poly acid chloride and poly acyl chloride are used indifferently in the present invention. The polyfunctional monomer used in the process according to the invention is present in amounts representing from 0.1 to 15%, preferably from 0.5 to 10% and more preferably from 0.8 to 6%, and even more preferably between 1 and 3% by weight based on the total amount of the oil phase.

According to a particular embodiment, the monomer added in step a) is at least one polyisocyanate having at least two isocyanate functional groups.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to an embodiment, the at least one polyisocyanate used in the process of the invention is present in amounts representing from 0.1 to 15%, preferably from 0.5 to 10% and more preferably from 0.8 to 6%, and even more preferably between 1 and 3% by weight based on the total amount of the oil phase.

Hydrophobic material: According to an embodiment, the hydrophobic material is an active ingredient.

Active ingredients used in the present invention are preferably chosen from the group consisting of flavor, flavor ingredients, perfume, perfume ingredients, nutraceuticals, cosmetics, insect control agents, biocide actives and mixtures thereof.

By "active ingredient", it is meant any active ingredient—single ingredient or a mixture of ingredients—which forms a two-phases dispersion when mixed with a solvent, for example water. The active ingredient of the present invention is hydrophobic.

Active ingredients are preferably chosen from the group consisting of flavor, flavor ingredients, perfume, perfume ingredients, nutraceuticals, cosmetics, pest control agents, biocide actives and mixtures thereof.

According to a particular embodiment, the active ingredient comprises a mixture of a perfume with another ingredient selected from the group consisting of nutraceuticals, cosmetics, pest control agents and biocide actives.

According to a particular embodiment, the active ingredient comprises a mixture of biocide actives with another ingredient selected from the group consisting of perfume, nutraceuticals, cosmetics, pest control agents.

According to a particular embodiment, the active ingredient comprises a mixture of pest control agents with another ingredient selected from the group consisting of perfume, nutraceuticals, cosmetics, biocide actives.

According to a particular embodiment, the active ingredient comprises a perfume.

According to a particular embodiment, the hydrophobic active ingredient consists of a perfume.

According to a particular embodiment, the active ingredient consists of biocide actives.

According to a particular embodiment, the active ingredient consists of pest control agents.

By "perfume" (or also "perfume oil") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, pest control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The term "biocide" refers to a chemical substance capable of killing living organisms (e.g. microorganisms) or reducing or preventing their growth and/or accumulation. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

As used herein, a "pest control agent" indicates a substance that serves to repel or attract pests, to decrease, inhibit or promote their growth, development or their activity. Pests refer to any living organism, whether animal, plant or fungus, which is invasive or troublesome to plants or animals, pests include insects notably arthropods, mites, spiders, fungi, weeds, bacteria and other microorganisms.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one $C_7$ to $C_{20}$ ring structure;

Group 7: perfuming ingredients having a logP value above 3.5 and comprising at least one tert-butyl or at least one trichloromethyl substitutent;

Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, Romascone® (methyl 2,2-dimethyl-6-methylene-1-cyclohexanecarboxylate, origin: Firmenich SA, Geneva, Switzerland), nerone, terpineol, dihydroterpineol, terpenyl acetate, dihydroterpenyl acetate, dipentene, eucalyptol, hexylate, rose oxide, Perycorolle® ((S)-1,8-p-menthadiene-7-ol, origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, Doremox® (tetrahydro-4-methyl-2-phenyl-2H-pyran, origin: Firmenich SA, Geneva, Switzerland), cyclohexyl acetate, cyclanol acetate, Fructalate® (1,4-cyclohexane diethyldicarboxylate, origin: Firmenich SA, Geneva, Switzerland), Koumalactone® ((3ARS,6SR, 7ASR)-perhydro-3,6-dimethyl-benzo[B]furan-2-one, origin: Firmenich SA, Geneva, Switzerland), Natactone® ((6R)-perhydro-3,6-dimethyl-benzo[B]furan-2-one, origin: Firmenich SA, Geneva, Switzerland), 2,4,6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yl)-2-buten-1-ol (origin: Firmenich SA, Geneva, Switzerland), Polysantol®((1'R,E)-3,3-dimethyl-5-(2',2',3'-trimethyl-3'-cyclopenten-1'-yl)-4-penten-2-ol, origin: Firmenich SA, Geneva, Switzerland), fleuramone, Hedione® HC (methyl-cis-3-oxo-2-pentyl-1-cyclopentane acetate, origin: Firmenich SA, Geneva, Switzerland), Veloutone® (2,2,5-Trimethyl-5-pentyl-1-cyclopentanone, origin: Firmenich SA, Geneva, Switzerland), Nirvanol® (3,3-dimethyl-5-(2,2,3-trimethyl-3-cyclopenten-1-yl)-4-penten-2-ol, origin: Firmenich SA, Geneva, Switzerland), 3-methyl-5-(2,2,3-trimethyl-3-cyclopenten-1-yl)-2-pentanol (origin, Givaudan SA, Vernier, Switzerland);

Group 3: damascones, Neobutenone® (1-(5,5-dimethyl-1-cyclohexen-1-yl)-4-penten-1-one, origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, Dynascone® (mixture of 1-(5,5-dimethyl-1-cyclohexen-1-yl)-4-penten-1-one and 1-(3,3-dimethyl-1-cyclohexen-1-yl)-4-penten-1-one, origin: Firmenich SA, Geneva, Switzerland), Dorinone® beta (1-(2,6,6-trimethyl-1-cyclohexen-1-yl)-2-buten-1-one, origin: Firmenich SA, Geneva, Switzerland), Romandolide® ((1S,1'R)-[1-(3',3'-Dimethyl-1'-cyclohexyl)ethoxycarbonyl]methyl propanoate, origin: Firmenich SA, Geneva, Switzerland), 2-tert-butyl-1-cyclohexyl acetate (origin: International Flavors and Fragrances, USA), Limbanol® (1-(2,2,3,6-tetramethyl-cyclohexyl)-3-hexanol, origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, Lorysia® (4-(1,1-dimethylethyl)-1-cyclohexyl acetate, origin: Firmenich SA, Geneva, Switzerland), 8-methoxy-1-p-menthene, Helvetolide® ((1S,1'R)-2-[1-(3',3'-dimethyl-1'-cyclohexyl) ethoxy]-2-methylpropyl propanoate, origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), Verdylate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), Hivernal® (a mixture of 3-(3,3-dimethyl-5-indanyl)propanal and 3-(1,1-dimethyl-5-indanyl)propanal, origin: Firmenich SA, Geneva, Switzerland), Rhubofix® (3',4-dimethyl-tricyclo[6.2.1.0(2,7)]undec-4-ene-9-spiro-2'-oxirane, origin: Firmenich SA, Geneva, Switzerland), 9/10-ethyldiene-3-oxatricyclo[6.2.1.0(2,7)]undecane, Polywood® (perhydro-5,5,8A-trimethyl-2-naphthalenyl acetate, origin: Firmenich SA, Geneva, Switzerland), octalynol, Cetalox® (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, camphopinene, cedramber (8-methoxy-2,6,6,8-tetramethyl-tricyclo[5.3.1.0(1,5)]undecane, origin: Firmenich SA, Geneva, Switzerland), cedrene, cedrenol, cedrol, Florex® (mixture of 9-ethylidene-3-oxatricyclo[6.2.1.0(2,7)]undecan-4-one and 10-ethylidene-3-oxatricyclo[6.2.1.0(2,7)]undecan-4-one, origin: Firmenich SA, Geneva, Switzerland), 3-methoxy-7,7-dimethyl-10-methylene-bicyclo[4.3.1]decane (origin: Firmenich SA, Geneva, Switzerland);

Group 6: Cedroxyde® (trimethyl-13-oxabicyclo-[10.1.0]-trideca-4,8-diene, origin: Firmenich SA, Geneva, Switzerland), Ambrettolide LG ((E)-9-hexadecen-16-olide, origin: Firmenich SA, Geneva, Switzerland), Habanolide® (pentadecenolide, origin: Firmenich SA, Geneva, Switzerland), muscenone (3-methyl-(4/5)-cyclopentadecenone, origin: Firmenich SA, Geneva, Switzerland), muscone (origin: Firmenich SA, Geneva, Switzerland), Exaltolide® (pentadecanolide, origin: Firmenich SA, Geneva, Switzerland), Exaltone® (cyclopentadecanone, origin: Firmenich SA, Geneva, Switzerland), (1-ethoxyethoxy)cyclododecane (origin: Firmenich SA, Geneva, Switzerland), Astrotone, 4,8-cyclododecadien-1-one;

Group 7: Lilial® (origin: Givaudan SA, Vernier, Switzerland), rosinol.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a logP above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols. According to another embodiment, the oil-based core comprises:

25-100 wt % of a perfume oil comprising at least 15 wt % of high impact perfume raw materials having a Log T<−4, and 0-75 wt % of a density balancing material having a density greater than 1.07 g/cm$^3$.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multi-dimensional Visualization of Physical and Perceptual Data Leading to a Creative Approach in Fragrance Development, Perfume & Flavorist, Vol. 33, September, 2008, pages 54-61. The nature of high impact perfume raw materials having a Log T<−4 and density balancing material having a density greater than 1.07 $g/cm^3$ are described in WO2018115250, the content of which are included by reference.

According to an embodiment, the high impact perfume raw materials having a Log T<−4 are selected from the list in Table A below.

TABLE A high impact perfume raw materials having a Log T < −4
Perfume raw materials (Log T < −4)

(+−)-1-METHOXY-3-HEXANETHIOL
4-(4-HYDROXY-1-PHENYL)-2-BUTANONE
(+−)-2-(4-METHYL-3-CYCLOHEXEN-1-YL)-2-PROPANETHIOL
2-METHOXY-4-(1-PROPENYL)-1-PHENYL ACETATE
PYRAZOBUTYLE
3-PROPYLPHENOL
1-(3-METHYL-1-BENZOFURAN-2-YL)ETHANONE
2-(3-PHENYLPROPYL)PYRIDINE
1-(3,3-DIMETHYL-1-CYCLOHEXEN-1-YL)-4-PENTEN-1-ONE (A) +
1-(5,5-DIMETHYL-1-CYCLOHEXEN-1-YL)-4-PENTEN-1-ONE (B)
1-(5,5-DIMETHYL-1-CYCLOHEXEN-1-YL)-4-PENTEN-1-ONE
(3RS,3ARS,6SR,7ASR)-PERHYDRO-3,6-DIMETHYL-
BENZO[B]FURAN-2-ONE (A) + (3SR,3ARS,6SR,7ASR)-
PERHYDRO-3,6-DIMETHYL-BENZO[B]FURAN-2-ONE (B)
(+−)-1-(5-ETHYL-5-METHYL-1-CYCLOHEXEN-1-YL)-4-PENTEN-
1-ONE
(1'S,3'R)-1-METHYL-2-[(1',2',2'-
TRIMETHYLBICYCLO[3.1.0]HEX-3'-
YL)METHYL]CYCLOPROPYL}METHANOL
(+−)-3-MERCAPTOHEXYL ACETATE
(2E)-1-(2,6,6-TRIMETHYL-1,3-CYCLOHEXADIEN-1-YL)-2-
BUTEN-1-ONE
7-METHYL-2H-1,5-BENZODIOXEPIN-3(4H)-ONE
(2E,6Z)-2,6-NONADIEN-1-OL
(4Z)-4-DODECENAL
(+−)-4-HYDROXY-2,5-DIMETHYL-3(2H)-FURANONE
METHYL 2,4-DIHYDROXY-3,6-DIMETHYLBENZOATE
3-METHYLINDOLE
(+−)-PERHYDRO-4ALPHA,8ABETA-DIMETHYL-4A-
NAPHTHALENOL
PATCHOULOL
2-METHOXY-4-(1-PROPENYL)PHENOL
(+−)-5,6-DIHYDRO-4-METHYL-2-PHENYL-2H-PYRAN (A) +
TETRAHYDRO-4-METHYLENE-2-PHENYL-2H-PYRAN (B)
4-METHYLENE-2-PHENYLTETRAHYDRO-2H-PYRAN (A) +
(+−)-4-METHYL-2-PHENYL-3,6-DIHYDRO-2H-PYRAN (B)
4-HYDROXY-3-METHOXYBENZALDEHYDE
NONYLENIC ALDEHYDE

TABLE A-continued high impact perfume raw materials having a Log T < −4
Perfume raw materials (Log T < −4)

2-METHOXY-4-PROPYLPHENOL
(2Z)-3-METHYL-5-PHENYL-2-PENTENENITRILE (A) + (2E)-3-
METHYL-5-PHENYL-2-PENTENENITRILE (B)
1-(SPIRO[4.5]DEC-6-EN-7-YL)-4-PENTEN-1-ONE (A) +
1-(SPIRO[4.5]DEC-7-EN-7-YL)-4-PENTEN-1-ONE (B)
2-METHOXYNAPHTHALENE
(−)-(3AR,5AS,9AS,9BR)-3A,6,6,9A-
TETRAMETHYLDODECAHYDRONAPHTHO[2,1-B]FURAN
5-NONANOLIDE
(3AR,5AS,9AS,9BR)-3A,6,6,9A-
TETRAMETHYLDODECAHYDRONAPHTHO[2,1-B]FURAN
7-ISOPROPYL-2H,4H-1,5-BENZODIOXEPIN-3-ONE
COUMARIN
4-METHYLPHENYL ISOBUTYRATE
(2E)-1-(2,6,6-TRIMETHYL-1,3-CYCLOHEXADIEN-1-YL)-2-
BUTEN-1-ONE
BETA,2,2,3-TETRAMETHYL-DELTA-METHYLENE-3-
CYCLOPENTENE-1-BUTANOL
DELTA DAMASCONE ((2E)-1-[(1RS,2SR)-2,6,6-TRIMETHYL-3-
CYCLOHEXEN-1-YL]-2-BUTEN-1-ONE)
(+−)-3,6-DIHYDRO-4,6-DIMETHYL-2-PHENYL-2H-PYRAN
ANISALDEHYDE
PARACRESOL
3-ETHOXY-4-HYDROXYBENZALDEHYDE
METHYL 2-AMINOBENZOATE
ETHYL METHYLPHENYLGLYCIDATE
OCTALACTONE G
ETHYL 3-PHENYL-2-PROPENOATE
(−)-(2E)-2-ETHYL-4-[(1R)-2,2,3-TRIMETHYL-3-
CYCLOPENTEN-1-YL]-2-BUTEN-1-OL
PARACRESYL ACETATE
DODECALACTONE
TRICYCLONE
(+)-(3R,5Z)-3-METHYL-5-CYCLOPENTADECEN-1-ONE
UNDECALACTONE
(1R,4R)-8-MERCAPTO-3-P-MENTHANONE
(3S,3AS,6R,7AR)-3,6-DIMETHYLHEXAHYDRO-1-BENZOFURAN-
2(3H)-ONE
BETA IONONE
(+−)-6-PENTYLTETRAHYDRO-2H-PYRAN-2-ONE
(3E,5Z)-1,3,5-UNDECATRIENE
10-UNDECENAL (A) + (9E)-9-UNDECENAL (B) +
(9Z)-9-UNDECENAL (C)
(Z)-4-DECENAL
(+−)-ETHYL 2-METHYLPENTANOATE
1,2-DIALLYLDISULFANE
(2Z)-2-TRIDECENENITRILE (A) + (3Z)-3-TRIDECENENITRILE (B) +
(3E)-3-TRIDECENENITRILE (C) + (2E)-2-TRIDECENENITRILE (D)
(+−)-2-ETHYL-4,4-DIMETHYL-1,3-OXATHIANE
(+)-(3R,5Z)-3-METHYL-5-CYCLOPENTADECEN-1-ONE
3-(4-TERT-BUTYLPHENYL)PROPANAL
ALLYL (CYCLOHEXYLOXY)ACETATE
METHYLNAPHTHYLKETONE
(+−)-(4E)-3-METHYL-4-CYCLOPENTADECEN-1-ONE (A) +
(+−)-(5E)-3-METHYL-5-CYCLOPENTADECEN-1-ONE (B) +
(+−)-(5Z)-3-METHYL-5-CYCLOPENTADECEN-1-ONE (C)
CYCLOPROPYLMETHYL (3Z)-3-HEXENOATE (A) +
CYCLOPROPYLMETHYL (3E)-3-HEXENOATE (B)
(4E)-4-METHYL-5-(4-METHYLPHENYL)-4-PENTENAL
(+−)-1-(5-PROPYL-1,3-BENZODIOXOL-2-YL)ETHANONE
4-METHYL-2-PENTYLPYRIDINE
(+−)-(E)-3-METHYL-4-(2,6,6-TRIMETHYL-2-CYCLOHEXEN-
1-YL)-3-BUTEN-2-ONE
(3ARS,5ASR,9ASR,9BRS)-3A,6,6,9A-
TETRAMETHYLDODECAHYDRONAPHTHO[2,1-B]FURAN
(2S,5R)-5-METHYL-2-(2-PROPANYL)CYCLOHEXANONE OXIME
6-HEXYLTETRAHYDRO-2H-PYRAN-2-ONE
(+−)-3-(3-ISOPROPYL-1-PHENYL)BUTANAL
METHYL 2-((1RS,2RS)-3-OXO-2-
PENTYLCYCLOPENTYL)ACETATE (A) + METHYL 2-
((1RS,2SR)-3-OXO-2-PENTYLCYCLOPENTYL)ACETATE (B)
1-(2,6,6-TRIMETHYL-1-CYCLOHEX-2-ENYL)PENT-1-EN-3-ONE
INDOL
7-PROPYL-2H,4H-1,5-BENZODIOXEPIN-3-ONE
ETHYL PRALINE
(4-METHYLPHENOXY)ACETALDEHYDE
ETHYL TRICYCLO[5.2.1.0.(2,6)]DECANE-2-CARBOXYLATE

TABLE A-continued high impact perfume raw materials having a Log T < −4
Perfume raw materials (Log T < −4)

(+)-(1'S,2S,E)-3,3-DIMETHYL-5-(2',2',3'-TRIMETHYL-3'-CYCLOPENTEN-1'-YL)-4-PENTEN-2-OL
(2R,4E)-3,3-DIMETHYL-5-[(1R)-2,2,3-TRIMETHYL-3-CYCLOPENTEN-1-YL]-4-PENTEN-2-OL (A) + (2S,4E)-3,3-DIMETHYL-5-[(1R)-2,2,3-TRIMETHYL-3-CYCLOPENTEN-1-YL]-4-PENTEN-2-OL (B)
8-ISOPROPYL-6-METHYL-BICYCLO[2.2.2]OCT-5-ENE-2-CARBALDEHYDE
METHYLNONYLACETALDEHYDE
4-FORMYL-2-METHOXYPHENYL 2-METHYLPROPANOATE
(E)-4-DECENAL
(+−)-2-ETHYL-4-(2,2,3-TRIMETHYL-3-CYCLOPENTEN-1-YL)-2-BUTEN-1-OL
(1R,5R)-4,7,7-TRIMETHYL-6-THIABICYCLO[3.2.1]OCT-3-ENE (A) + (1R,4R,5R)-4,7,7-TRIMETHYL-6-THIABICYCLO[3.2.1]OCTANE (B)
(−)-(3R)-3,7-DIMETHYL-1,6-OCTADIEN-3-OL
(E)-3-PHENYL-2-PROPENENITRILE
4-METHOXYBENZYL ACETATE
(E)-3-METHYL-5-(2,2,3-TRIMETHYL-3-CYCLOPENTEN-1-YL)-4-PENTEN-2-OL
ALLYL (3-METHYLBUTOXY)ACETATE (A) + (+−)-ALLYL (2-METHYLBUTOXY)ACETATE
(+−)-(2E)-1-(2,6,6-TRIMETHYL-2-CYCLOHEXEN-1-YL)-2-BUTEN-1-ONE
(1E)-1-(2,6,6-TRIMETHYL-1-CYCLOHEXEN-1-YL)-1-PENTEN-3-ONE

According to an embodiment, perfume raw materials having a Log T<−4 are chosen in the group consisting of aldehydes, ketones, alcohols, phenols, esters lactones, ethers, epoxydes, nitriles and mixtures thereof.

According to an embodiment, perfume raw materials having a Log T<−4 comprise at least one compound chosen in the group consisting of alcohols, phenols, esters lactones, ethers, epoxydes, nitriles and mixtures thereof, preferably in amount comprised between 20 and 70% by weight based on the total weight of the perfume raw materials having a Log T<−4.

According to an embodiment, perfume raw materials having a Log T<−4 comprise between 20 and 70% by weight of aldehydes, ketones, and mixtures thereof based on the total weight of the perfume raw materials having a Log T<−4.

The remaining perfume raw materials contained in the oil-based core may have therefore a Log T>−4.

Non limiting examples of perfume raw materials having a Log T>−4 are listed in table B below.

TABLE B perfume raw materials having a Log T > −4
Perfume raw materials (Log T > −4)

ETHYL 2-METHYLBUTYRATE
(E)-3-PHENYL-2-PROPENYL ACETATE
(+−)-8-SEC-BUTYLQUINOLINE (A) + (+−)-6-SEC-BUTYLQUINOLINE
(+−)-3-(1,3-BENZODIOXOL-5-YL)-2-METHYLPROPANAL
VERDYL PROPIONATE
1-(OCTAHYDRO-2,3,8,8-TETRAMETHYL-2-NAPHTALENYL)-1-ETHANONE
METHYL 2-((1RS,2RS)-3-OXO-2-PENTYLCYCLOPENTYL)ACETATE
(+−)-(E)-4-METHYL-3-DECEN-5-OL
2,4-DIMETHYL-3-CYCLOHEXENE-1-CARBALDEHYDE
1,3,3-TRIMETHYL-2-OXABICYCLO[2.2.2]OCTANE
TETRAHYDRO-4-METHYL-2-(2-METHYL-1-PROPENYL)-2H-PYRAN
ALDEHYDE C 12
1-OXA-12-CYCLOHEXADECEN-2-ONE (A) + 1-OXA-13-CYCLOHEXADECEN-2-ONE (B)
(+−)-3-(4-ISOPROPYLPHENYL)-2-METHYLPROPANAL
ALDEHYDE C 11 LENIQUE
(+−)-2,6-DIMETHYL-7-OCTEN-2-OL
(+−)-2,6-DIMETHYL-7-OCTEN-2-OL
ALLYL 3-CYCLOHEXYLPROPANOATE
(Z)-3-HEXENYL ACETATE
(2RS,5SR)-5-METHYL-2-(2-PROPANYL)CYCLOHEXANONE (A) + (2RS,5RS)-5-METHYL-2-(2-PROPANYL)CYCLOHEXANONE (B)
ALLYL HEPTANOATE
(1RS,2RS)-2-(2-METHYL-2-PROPANYL)CYCLOHEXYL ACETATE (A) + (1RS,2SR)-2-(2-METHYL-2-PROPANYL)CYCLOHEXYL ACETATE (B)
1,1-DIMETHYL-2-PHENYLETHYL BUTYRATE
GERANYL ACETATE (A) + NERYL ACETATE (B)
(+−)-1-PHENYLETHYL ACETATE
1,1-DIMETHYL-2-PHENYLETHYL ACETATE
3-METHYL-2-BUTENYL ACETATE
ETHYL 3-OXOBUTANOATE (A) <=> (2Z)-ETHYL 3-HYDROXY-2-BUTENOATE (B)
8-P-MENTHANOL
8-P-MENTHANYL ACETATE (A) + 1-P-MENTHANYL ACETATE (B)
(+−)-2-(4-METHYL-3-CYCLOHEXEN-1-YL)-2-PROPANYL ACETATE
(+−)-2-METHYLBUTYL BUTANOATE
2-{(1S)-1-[(1R)-3,3-DIMETHYLCYCLOHEXYL]ETHOXY}-2-OXOETHYL PROPIONATE
3,5,6-TRIMETHYL-3-CYCLOHEXENE-1-CARBALDEHYDE (A) + 2,4,6-TRIMETHYL-3-CYCLOHEXENE-1-CARBALDEHYDE (B)
2-CYCLOHEXYLETHYL ACETATE
ALDEHYDE C 8
ETHYL BUTANOATE
(+−)-(3E)-4-(2,6,6-TRIMETHYL-2-CYCLOHEXEN-1-YL)-3-BUTEN-2-ONE (A) + (3E)-4-(2,6,6-TRIMETHYL-1-CYCLOHEXEN-1-YL)-3-BUTEN-2-ONE (B);
1-[(1RS,6SR)-2,2,6-TRIMETHYLCYCLOHEXYL]-3-HEXANOL
1,3,3-TRIMETHYL-2-OXABICYCLO[2.2.2]OCTANE
1,3,3-TRIMETHYL-2-OXABICYCLO[2.2.2]OCTANE
ETHYL HEXANOATE
UNDECANAL
ALDEHYDE C 10
2-PHENYLETHYL ACETATE
(1S,2S,4S)-1,7,7-TRIMETHYLBICYCLO[2.2.1]HEPTAN-2-OL (A) + (1S,2R,4S)-1,7,7-TRIMETHYLBICYCLO[2.2.1]HEPTAN-2-OL (B)
(+−)-3,7-DIMETHYL-3-OCTANOL
1-METHYL-4-(2-PROPANYLIDENE)CYCLOHEXENE
(+)-(R)-4-(2-METHOXYPROPAN-2-YL)-1-METHYLCYCLOHEX-1-ENE
VERDYL ACETATE
(3R)-1-[(1R,6S)-2,2,6-TRIMETHYLCYCLOHEXYL]-3-HEXANOL (A) + (3S)-1-[(1R,6S)-2,2,6-

TABLE B-continued perfume raw materials having a Log T > −4
Perfume raw materials (Log T > −4)

TRIMETHYLCYCLOHEXYL]-3-
HEXANOL (B) + (3R)-1-[(1S,6S)-2,2,6-
TRIMETHYLCYCLOHEXYL]-3-
HEXANOL (C)
(+)-(1S,1'R)-2-[1-(3',3'-DIMETHYL-1'-
CYCLOHEXYL)ETHOXY]-2-
METHYLPROPYL PROPANOATE

According to an embodiment, the oil-based core comprises 2-75 wt % of a density balancing material having a density greater than 1.07 g/cm$^3$ and 25-98 wt % of a perfume oil comprising at least 15 wt % of high impact perfume raw materials having a Log T<−4. The density of a component is defined as the ratio between its mass and its volume (g/cm$^3$).

Several methods are available to determine the density of a component.

One may refer for example to the ISO 298:1998 method to measure d20 densities of essential oils.

According to an embodiment, the density balancing material is chosen in the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

According to a particular embodiment, the density balancing material is chosen in the group consisting of benzyl salicylate, benzyl benzoate, cyclohexyl salicylate and mixtures thereof.

According to another embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4 butanediol, benzyl alcohol, triethyl citrate, triacetin, benzyl acetate, ethyl acetate, propylene glycol (1,2-propanediol), 1,3-Propanediol, dipropylene glycol, glycerol, glycol ethers and mixtures thereof.

According to any one of the invention's embodiments, the hydrophobic material represents between about 10% and 60% w/w, or even between 20% and 45% w/w, by weight, relative to the total weight of the emulsion as obtained after step b).

According to a particular embodiment, the oil phase essentially consists of the polyisocyanate with at least 3 isocyanate functional groups, and a perfume or flavor oil.

In another step of the process according to the invention, the oil phase of step a) is dispersed into an aqueous solution comprising a polysuccinimide derivative to form an oil-in-water emulsion. The polysuccinimide derivative according to the invention is used as an emulsifier.

The mean droplet size of the emulsion is preferably comprised between 1 and 1000 microns, more preferably between 1 and 500 microns, and even more preferably between 5 and 50 microns.

The polysuccinimide derivative used in the invention is preferably obtained by grafting at least one amine to at least one succinimide repeating unit.

According to a particular embodiment, the polysuccinimide derivative is obtained by grafting successively two amines to the polysuccinimide.

Once the at least amine is grafted on the polysuccinimide, said resulting polysuccinimide derivative can be subjected to an hydrolysis before introducing it in water to form the aqueous phase and/or when introducing in water to form the aqueous phase.

According to a particular embodiment, the hydrolysis step takes place when the polysuccinimide is in contact with water to form the aqueous phase.

Any functional amine can be grafted, preferably monofunctional amine or amino acid to prevent cross-linking.

According to an embodiment, functional mono or polyamines that can be grafted on succinimide repeating unit have the following structures:

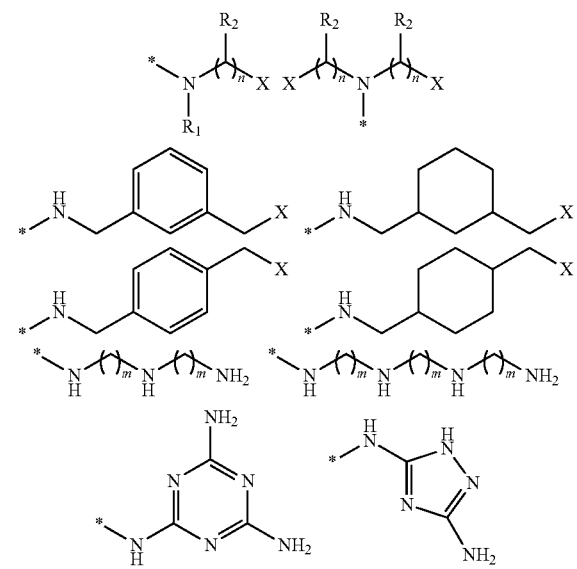

$R_1, R_2$ = H or Me, Et
X = Me, OH, NH$_2$, SH, N$^+$(R$_1$)$_3$, SO$_3$Na, CO$_2$H, CO$_2$Na
n = 2-17
m = 2-4

Amino acids can also be grafted on the succinimide repeating units. Amino acids that can be used in the present invention have the following structures:

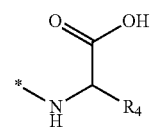

Where

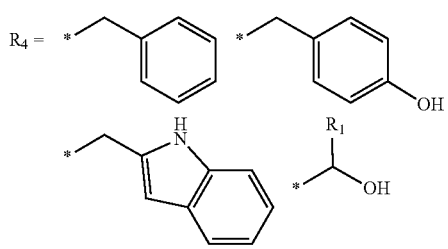

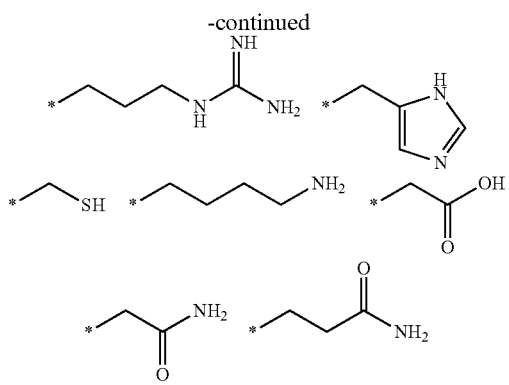

According to an embodiment, the amine is chosen in the group consisting of n-alkyl amine, hydroxyl alkyl amine, M-type Jeffamine®, amino acids, dopamine, DOPA and mixtures thereof.

According to a particular embodiment, the amine is chosen in the group consisting of 1-Dodecylamine (DDA), 1-decylamine, dopamine, 2-aminoethan-1-ol, 3-amino-propan-1-ol, 6-amino-hexan-1-ol and mixtures thereof.

According to a particular embodiment, the polysuccinimide is modified with at least two amines, preferably chosen in the group consisting of 1-Dodecylamine (DDA), 1-decylamine, dopamine, 2-aminoethan-1-ol, 3-amino-propan-1-ol and 6-amino-hexan-1-ol.

The polysuccinimide derivative is preferably chosen in the group consisting of polysuccinimide-co-poly(n-ethylaspartamide), polysuccinimide-co-poly(n-butylaspartamide), polysuccinimide-co-poly(n-hexylaspartamide), polysuccinimide-co-poly(n-dodecylaspartamide), polysuccinimide-co-poly(n-dodecylaspartamide)-co-poly(3,4-dihydroxybenzylaspartamide), and mixtures thereof.

It should be noted that when the above compounds are dissolved in water, they form respectively compounds chosen in the group consisting in poly(aspartic acid)-co-poly (n-ethylaspartamide), poly(aspartic acid)-co-poly(n-butylaspartamide), poly(aspartic acid)-co-poly(n-hexylaspartamide), poly(aspartic acid)-co-poly(n-dodecylaspartamide), poly(aspartic acid)-co-poly(n-dodecylaspartamide)-co-poly(3,4-dihydroxybenzylaspartamide) and mixtures thereof.

According to an embodiment, the polysuccinimide derivative is obtained by the following process:
a) polycondensation of aspartic acid in the presence of acid catalyst to obtain a polysuccinimide;
b) addition of at least one amine to the polysuccinimide of step a) to obtain a polysuccinimide derivative;
c) optionally, hydrolysis of polysuccinimide derivative in water.

According to a particular embodiment, the acid catalyst is phosphoric acid or adipic acid.

According to a particular embodiment, the polysuccinimide derivative is a polysuccinimide-co-poly(n-dodecylaspartamide) and is obtained by the following process:
a) polycondensation of aspartic acid in the presence of acid catalyst to obtain a polysuccinimide;
b) addition of n-dodecyl amine to the polysuccinimide of step a) to obtain a polysuccinimide derivative;
c) optionally, hydrolysis of polysuccinimide derivative in water.

According to a particular embodiment, the polysuccinimide derivative is a polysuccinimide-co-poly(n-dodecylaspartamide)-co-poly(3,4-dihydroxybenzylaspartamide) and is obtained by the following process:
a) polycondensation of aspartic acid in the presence of acid catalyst to obtain a polysuccinimide;
b) addition of n-dodecyl amine to the polysuccinimide of step a) to obtain poly(succinimide-co-n-dodecylaspartamide);
c) addition of dopamine on compound obtained in step b) to obtain a polysuccinimide derivative; and
d) optionally, hydrolysis of polysuccinimide derivative in water.

The polysuccinimide can also be obtained by reactive extrusion, preferably in the presence of aliphatic diacids, such for example adipic acid.

According to an embodiment, when the polysuccinimide derivative is a polysuccinimide-co-poly(n-dodecylaspartamide)-co-poly(3,4-dihydroxybenzylaspartamide), the molar ratio between dopamine and 1-dodecylamine is comprised between 0.5 and 8, preferably between 1 and 4. The polysuccinimide derivative is preferably used in an amount comprised between 0.1 and 5% by weight, more preferably between 0.5 and 2.5% by weight, relative to the total weight of the emulsion obtained in step b).

The nature of the shell depends on the nature of the monomer present in the oil phase and the optional reactant present in the aqueous phase.

Thus, according to an embodiment, microcapsules according to the present invention are polyurea-based capsules. The polysuccinimide derivatives of the present invention were surprisingly highly compatible with the polyurea shell of microcapsules. Indeed, to the best of the inventor's knowledge, polyurea and polysuccinimide are not thermodynamically compatible According to this particular embodiment, interfacial polymerization may be induced by addition of a polyamine reactant in the aqueous phase to form a polyurea wall with a polyisocyanate present in the oil phase. The amine is preferably chosen in the group consisting of guanidine salts, tris-(2-aminoethyl)amine, N,N,N',N'-tetrakis(3-aminopropyl)-1,4-butanediamine, guanazole, aminoacids such as lysine, aminoalcohol such as 2-amino-1,3-propanediol, ethanolamine and mixtures thereof.

According to another embodiment, polyurea-based capsules are formed in absence of added polyamine reactant, and result only from the autopolymerization of the at least one polyisocyanate.

According to another embodiment, microcapsules according to the present invention are polyurethane-based capsules. According to this particular embodiment, interfacial polymerization is induced by the presence of a polyol in the aqueous phase.

Preferably the polyol reactant is selected from the group consisting of monomeric and polymeric polyols with multiple hydroxyl groups available for reaction and mixtures thereof.

According to another embodiment, capsules according to the present invention are polyurea/polyurethane based. In that case interfacial polymerization is induced by addition of a mixture of the reactant mentioned under both precedent embodiments. Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to another embodiment, microcapsules according to the present invention are polyamide-based capsules. According to this particular embodiment, interfacial polymerization is induced by addition of a polyamine reactant in the aqueous phase to form a polyamide wall with a poly acid chloride present in the oil phase.

This is followed by a curing step c) which allows ending up with microcapsules in the form of a slurry. According to a particular embodiment, said step is performed at a temperature comprised between 60 and 80° C., possibly under pressure, for 1 to 4 hours. More particularly, it is performed at between 50 and 90° C. for between 30 minutes and 4 hours.

According to the invention, the monomer reacts with the polysuccinimide derivative during the interfacial polymerisation (curing step) to form the microcapsules in the form of a slurry.

According to a particular embodiment of the invention, at the end of step c) one may also add to the invention's slurry a polymer selected from cationic polymer and mixtures thereof to form an outer coating to the microcapsules.

Cationic polymers are well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 1.5M Dalton. According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step c). It is clearly understood by a person skilled in the art that only part of said added polymers will be incorporated into/deposited on the microcapsule shell.

Another object of the invention is a process for preparing a microcapsule slurry comprising the steps as defined above and an additional step d) consisting of submitting the slurry obtained in step c) to a drying, like spray-drying, to provide the microcapsules as such, i.e. in a powdery form. It is understood that any standard method known by a person skilled in the art to perform such drying is also applicable. In particular the slurry may be spray-dried preferably in the presence of a polymeric carrier material such as polyvinyl acetate, polyvinyl alcohol, dextrins, natural or modified starch, vegetable gums, pectins, xanthans, alginates, carragenans or cellulose derivatives to provide microcapsules in a powder form.

However, one may cite also other drying method such as the extrusion, plating, spray granulation, the fluidized bed, or even a drying at room temperature using materials (carrier, desiccant) that meet specific criteria as disclosed in WO2017/134179.

According to a particular embodiment, the carrier material contains free perfume oil which can be the same or different from the perfume from the core of the microcapsules.

Microcapsule Slurry/Microcapsule Powder

Microcapsule slurry and microcapsule powder obtainable by the process as defined above are also an object of the invention.

Another object of the invention is a core-shell microcapsule slurry comprising at least one microcapsule made of an oil-based core comprising a hydrophobic material and a shell formed from the reaction between a polyfunctional monomer and a polysuccinimide derivative.

It should be understood that the core-shell microcapsules are dispersed in water in the microcapsule slurry as defined above.

Another object of the invention is a core-shell microcapsule comprising:
an oil-based core comprising a hydrophobic material, and
a shell formed from the reaction between a polyfunctional monomer and a polysuccinimide derivative.

All of the embodiments described previously for the process also apply for the microcapsules as defined above.

Microcapsules obtained by the process of the invention have a negative zeta potential, preferably comprised between −50 and −120 mV. A suitable apparatus for measuring the zeta potential is Zetasizer Nano ZS (Malvern Instruments). Without being bound by any theory, the inventors are of the opinion that the negative zeta potential comes from the presence of anionic polysuccinimide derivatives in the shell resulting in negative charges on the surface of the microcapsules. The negative surface of the microcapsules shows the benefit of better deposition for cationic polymers.

Perfuming Composition/Consumer Products

Another object of the present invention is a perfuming composition comprising:
(i) microcapsules as defined above, wherein the oil comprises a perfume;
(ii) at least one ingredient selected from the group consisting of a perfumery carrier, a perfumery co-ingredient and mixtures thereof;
(iii) optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to at least impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsules as defined above.

The invention's microcapsules can advantageously be used in many application fields and used in consumer products. Microcapsules can be used in liquid form applicable to liquid consumer products as well as in powder form, applicable to powder consumer products.

Another object of the invention is a consumer product comprising:
  a) a personal care active base, and
  b) microcapsules as defined above or the perfuming composition as defined above, wherein the consumer product is in the form of a personal care composition.

Personal care active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature. The personal care composition is preferably chosen in the group consisting of a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product) or a fine fragrance product (e.g. Eau de Toilette—EdT).

Another object of the invention is a consumer product comprising:
  a) a home care or a fabric care active base, and
  b) microcapsules as defined above or the perfuming composition as defined above,
wherein the consumer product is in the form of a home care or a fabric care composition.

Home care or fabric care bases in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature. The home or fabric care composition is preferably chosen in the group consisting fabric softener, liquid detergent, powder detergent, liquid scent booster solid scent booster.

According to a particular embodiment, the consumer product as defined above is liquid and comprises:
  a) from 2 to 65% by weight, relative to the total weight of the consumer product, of at least one surfactant;
  b) water or a water-miscible hydrophilic organic solvent; and
  c) microcapsule slurry as defined above,
  d) optionally non-encapsulated perfume.

According to a particular embodiment, the consumer product as defined above is in a powder form and comprises:
  (a) from 2 to 65% by weight, relative to the total weight of the consumer product, of at least one surfactant;
  (b) microcapsule powder as defined above.
  (c) optionally perfume powder that is different from the microcapsules defined above.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
  a) from 2 to 65% by weight, relative to the total weight of the consumer product, of at least one surfactant;
  b) water or a water-miscible hydrophilic organic solvent; and
  c) a perfuming composition as defined above is another object of the invention.

Also a powder consumer product comprising
 (a) from 2 to 65% by weight, relative to the total weight of the consumer product, of at least one surfactant; and
 (b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumed consumer product can be a perfume, such as a fine perfume, a cologne, an after-shave lotion, a body-splash; a fabric care product, such as a liquid or solid detergent, tablets and pods, a fabric softener, a dryer sheet, a fabric refresher, an ironing water, or a bleach; a personal-care product, such as a hair-care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.); a hygiene product such as sanitary napkins, diapers, toilet paper.

Preferably, the consumer product comprises from 0.05 to 15 wt %, preferably 0.1 to 15 wt %, more preferably between 0.2 and 5 wt % of the microcapsules of the present invention, these percentages being defined by weight relative to the total weight of the consumer product. Of course the above concentrations may be adapted according to the benefit effect desired in each product.

Fabric Softener

An object of the invention is a consumer product in the form of a fabric softener composition comprising:
 a fabric softener active base; preferably chosen in the group consisting of dialkyl quaternary ammonium salts, dialkyl ester quaternary ammonium salts (esterquats), Hamburg esterquat (HEQ), TEAQ (triethanolamine quat), silicones and mixtures thereof, preferably in an amount comprised between 85 and 99.95% by weight based on the total weight of the composition,
 a microcapsule slurry as defined above, preferably in an amount comprised between 0.05 to 15 wt %, more preferably between 0.1 and 5 wt % by weight based on the total weight of the composition.

Liquid Detergent

An object of the invention is a consumer product in the form of a liquid detergent composition comprising:
 a liquid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
 a microcapsule slurry as defined above, preferably in an amount comprised between 0.05 to 15 wt %, more preferably between 0.1 and 5 wt % by weight based on the total weight of the composition.

Solid Detergent

An object of the invention is a consumer product in the form of a solid detergent composition comprising:
 a solid detergent active base; preferably chosen in the group consisting of anionic surfactant such as alkylbenzenesulfonate (ABS), secondary alkyl sulfonate (SAS), primary alcohol sulfate (PAS), lauryl ether sulfate (LES), methyl ester sulfonate (MES) and nonionic surfactant such as alkyl amines, alkanolamide, fatty alcohol poly(ethylene glycol) ether, fatty alcohol ethoxylate (FAE), ethylene oxide (EO) and propylene oxide (PO) copolymers, amine oxydes, alkyl polyglucosides, alkyl polyglucosamides, preferably in an amount comprised between 85 and 99.95% by weight based on the total weight of the composition,
 a microcapsule powder or microcapsule slurry as defined above, preferably in an amount comprised between 0.05 to 15 wt %, more preferably between 0.1 and 5 wt % by weight based on the total weight of the composition.

Shampoo/Shower Gel

An object of the invention is a consumer product in the form of a shampoo or a shower gel composition comprising:
 a shampoo or a shower gel active base; preferably chosen in the group consisting of sodium alkylether sulfate, ammonium alkylether sulfates, alkylamphoacetate, cocamidopropyl betaine, cocamide MEA, alkylglucosides and aminoacid based surfactants and mixtures thereof, preferably in an amount comprised between 85 and 99.95% by weight based on the total weight of the composition,
 a microcapsule slurry as defined above, preferably in an amount comprised between 0.05 to 15 wt %, more preferably between 0.1 and 5 wt % by weight based on the total weight of the composition.

Rinse-Off Conditioner

An object of the invention is a consumer product in the form of a rinse-off conditioner composition comprising:
 a rinse-off conditioner active base; preferably chosen in the group consisting of cetyltrimonium chloride, stearyl trimonium chloride, benzalkonium chloride, behentrimonium chloride and mixture thereof, preferably in an amount comprised between 85 and 99.95% by weight based on the total weight of the composition, a microcapsule slurry as defined above, preferably in an amount comprised between 0.05 to 15 wt %, more preferably between 0.1 and 5 wt % by weight based on the total weight of the composition.

Hair Coloration

An object of the invention is a consumer product in the form of an oxidative hair coloring composition comprising:

an oxidizing phase comprising an oxidizing agent and an alkaline phase comprising an alkakine agent, a dye precursor and a coupling compound; wherein said dye precursor and said coupling compound form an oxidative hair dye in the presence of the oxidizing agent, preferably in an amount comprised between 85 and 99.95% by weight based on the total weight of the composition, a microcapsule slurry as defined above, preferably in an amount comprised between 0.05 to 15 wt %, more preferably between 0.1 and 5 wt % by weight based on the total weight of the composition.

By "oxidative hair coloring composition", it is meant a composition comprising two groups of colorless dye molecules: the dye precursor and the coupling agent. Upon reaction with each other through an oxidation process, they form a wide range of colored molecules (dyes) that are then trapped into the hair due their size. In other words, the dye precursor and the coupling compound form an oxidative hair dye in the presence of the oxidizing agent.

"Dye precursor" and "oxidative dye precursor" are used indifferently in the present invention.

Dye precursors can be aromatic compounds derived from benzene substituted by at least two electron donor groups such as $NH_2$ and OH in para or ortho positions to confer the property of easy oxidation.

According to an embodiment, dye precursors are chosen in the group consisting of p-phenylene diamine, 2,5-diamino toluene, N,N-bis(2-hydroxymethyl)-p-phenylene diamine, 4-aminophenol, 1,4-diamino-benzene, and mixtures thereof.

The primary dye precursors is used in combination with coupling agents. Coupling agents are preferably aromatic compounds derived from benzene and substituted by groups such as $NH_2$ and OH in the meta position and do not produce color singly, but which modify the color, shade or intensity of the colors developed by the dye precursor.

According to an embodiment, the coupling agent is chosen in the group consisting of resorcinol, 2-methyl resorcinol, 4-chlororesorchinol, 2,5-diamino-toluene, 1,3-diamino-benzene, 2,4-diaminophenoxyethanol HCl, 2-amino-hydroxyethylaminoanisole sulfate, 4-amino-2-hydroxytoluene, and mixtures thereof.

The oxidative dye precursor is preferably used in an amount comprised between 0.001% and 5%, preferably between 0.1% and 4% by weight based on the total weight of the composition.

The use of oxidative dye precursors and coupling agents in hair coloring formulation have been widely disclosed in the prior art and is well-known from the person skilled in the art. One may cite for example EP0946133A1, the content of which is incorporated by reference.

The alkaline phase comprises an alkaline agent, preferably chosen in the group consisting of ammonia hydroxide, ammonia carbonate, ethanolamine, potassium hydroxide, sodium borate, sodium carbonate, triethanolamine and mixtures thereof.

The alkaline agent is preferably used in an amount comprised between 1% and 10%, preferably between 3% and 9% by weight based on the total weight of the composition.

According to the invention, the coupling agent and the dye precursor in an alkaline medium form an oxidative hair dye in the presence of the oxidizing agent.

The oxidizing agent will supply the necessary oxygen gas to develop color molecules and create a change in hair color.

The oxidizing agent should be safe and effective for use in the compositions herein.

Preferably, the oxidizing agents suitable for use herein will be soluble in the compositions according to the present invention when in liquid form and/or in the form intended to be used.

Preferably, oxidizing agents suitable for use herein will be water-soluble. Suitable oxidizing agents for use herein are selected from inorganic peroxygen oxidizing agents, preformed organic peroxyacid oxidizing agents and organic peroxide oxidizing agents or mixtures thereof.

The oxidizing agent is preferably used in an amount comprised between 5 and 30%, preferably between 5 and 25% by weight based on the total weight of the composition.

Components commonly used in cosmetic compositions may be added into the hair coloring composition as defined in the present invention. One may cite for example, surfactants, cationic polymers, oily substances, silicone derivatives, free perfume, preservatives, ultraviolet absorbents, antioxidants, germicides, propellants, thickeners.

According to a particular embodiment, the hair coloring composition comprises one or more quaternary ammonium compounds, preferably chosen in the group consisting of cetyltrimonium chloride, stearyl trimonium chloride, benzalkonium chloride, behentrimonium chloride and mixture thereof to confer hair conditioner benefits.

Perfuming composition According to a particular embodiment, the consumer product is in the form of a perfuming composition comprising:

0.1 to 30%, preferably 0.1 to 20% of microcapsules as defined previously, 0 to 40%, preferably 3-40% of perfume, and 20-90%, preferably 40-90% of ethanol, by weight based on the total weight of the perfuming composition.

The invention will now be further described by way of examples. It will be appreciated that the invention as claimed is not intended to be limited in any way by these examples.

EXAMPLES

Example 1

Preparation of Polysuccinimide Derivatives
Preparation of polysuccinimide (PSI, 1)

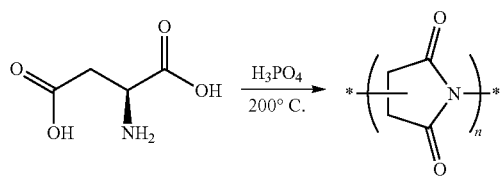

In a 250 ml, beaker, orthophosphoric acid (10 g, 0.114 mmol) and L-Aspartic Acid (100 g, 751 mmol) were respectively added and mixed in a mortar to give a white solid.

Solid was heated at 120° C. for 1 h under vacuum in a three-nicked reactor. Solid was crushed in a mortar and it was heated at 200° C. for additional 2 h 30 under vacuum. Resulting powder was washed 3 times with 500 mL of water, then with NaOH 30 wt % to obtain an aqueous phase at pH 4 after filtration. Solid was then dried under vacuum at 50° C. for at least 24 h.

Preparation of polysuccinimide-co-poly(n-dodecylaspartamide) (2)

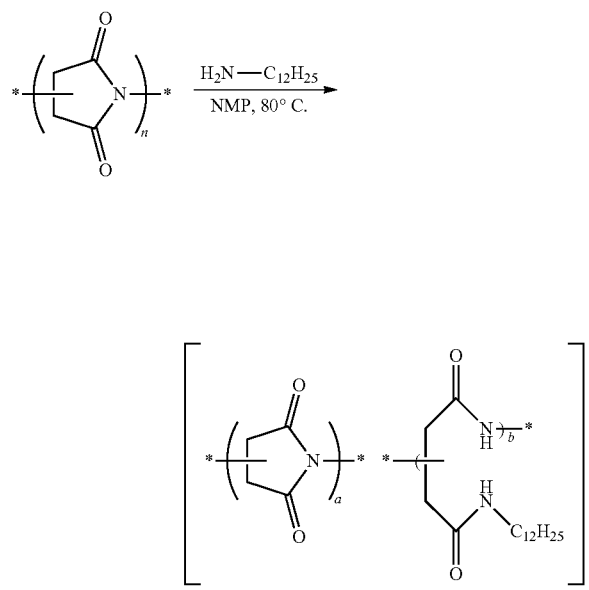

In a 250 mL round-bottomed flask, 1 (15 g, 155 mmol of repeating units) was dissolved in NMP (150 mL) and heated at 80° C. to give a yellow-orange solution. 1-Dodecylamine (DDA) (5, 10 or 20 mol % with respect to PSI repeating units) was added into the solution, in several fractions. The solution was heated at 80° C. for 24 h. The polymer was precipitated and washed in diethyl ether (600 mL). The solid was dried at 50° C. under vacuum for 24 h. Codes as PSI-X (X=5, 10 or 20), which mean the molar grafting ratio of DDA, denoted the samples in Table 1.

Preparation of polysuccinimide-co-poly(n-dodecylaspartamide)-co-poly(3,4-dihydroxybenzylaspartamide) (3)

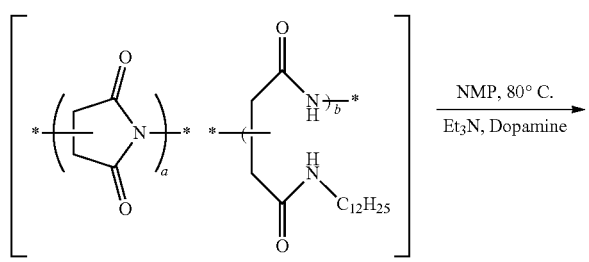

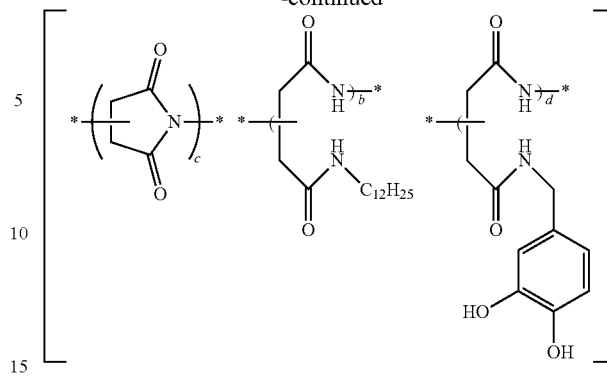

In a 100 ml, round-bottomed three-nicked flask, 2 (5 g) was added in NMP (50 mL) and heated at 80° C. to give a yellow-orange solution. DBU (10 mol %) and triethylamine (10-30 mol %) were added, under nitrogen flow. A solution of dopamine (10 to 30 mol % of PSI repeating units) in NMP (10 mL) was added dropwise and the reaction mixture was stirred at 80° C. for 20 h. Reaction mixture was slowly cooled to room temperature under stirring. Polymer was washed with n-heptane (350 mL) to give a biphasic mixture. The lower phase was precipitated in absolute ethanol (350 mL) or diethyl ether (350 mL) and filtered to give a solid, which was dried at 50° C. under vacuum. Codes as PSI-X-Y (Y=10, 20 or 30), which mean the molar grafting ratio of DDA and those of dopamine, denoted the samples in Table 1.

TABLE 1 copolymers composition

| Polymers | Cap-sules | Expected mol % (DDA) | Expected mol % (dopamine) | Measured by NMR (mol %) (DDA) | Measured by NMR (mol %) (dopamine) |
|---|---|---|---|---|---|
| PSI-5 | A | 5 | 0 | 4 | 0 |
| PSI-10 | B | 10 | 0 | 13 | 0 |
| PSI-20 | C | 20 | 0 | 22 | 0 |
| PSI-5-10 | D | 5 | 10 | 3 | 13 |
| PSI-5-20 | E | 5 | 20 | 4 | 25 |
| PSI-5-30 | F | 5 | 30 | 5 | 36 |
| PSI-10-10 | G | 10 | 10 | 8 | 9 |
| PSI-10-20 | H | 10 | 20 | 10 | 21 |
| PSI-10-30 | I | 10 | 30 | 8 | 34 |
| PSI-20-10 | J | 20 | 10 | 24 | 10 |
| PSI-20-20 | K | 20 | 20 | 23 | 21 |
| PSI-20-30 | L | 20 | 30 | 21 | 34 |

For optical microscope observations, a fluorescent marker (1-pyrenemethylamine) is grafted on polysuccinimide derivatives (2) and (3) prepared above.

In a 25 mL round-bottomed three-nicked flask, the different copolymers (0.5 g) were dissolved in NMP (5 mL) and heated at 80° C. to give an orange-brown solution. Triethylamine (0.1 mL) was added into the solution. 1-Pyrenemethylamine hydrochloride (7.65 mg, 0.029 mmol) was dissolved in the minimum of NMP and was added to the reaction mixture. The solution was heated at 80° C. for 10 h. The reaction mixture was slowly cooled to room temperature under stirring. Polymer was washed with n-heptane (100 mL) to give a biphasic mixture. The lower phase was precipitated in absolute ethanol or diethyl ether and filtered to give a solid, which was dried at 50° C. under vacuum.

Example 2

Preparation of Microcapsules According to the Invention

Desmodur® N-100 (4.76 g, 24.5 mmol NCO) and Acridine (0.25 g—compound added to follow the deposition) were diluted into the perfume oil (20.74 g, Table 2). The copolymer 2 or 3 (0.7 g) were diluted into an aqueous buffered solution at pH 7 (31.57 g). The oil and aqueous phases were mixed together, and then dispersed with Ultra Turax for 3 min at 24 000 rpm. The emulsion was put into a 250 mL glass double jacketed reactor and agitated at 350 rpm at room temperature. A solution of guanidine carbonate (24.5 mmol) into an aqueous buffered solution at pH 7 (10.85 g) was added dropwise into the emulsion for 1 h. Then, the temperature of the reaction mixture was slowly increased from room temperature to 70° C. in 4 times every 15 minutes (RT; 40° C.; 50° C.; 60° C.; 70° C.) and then kept at 70° C. for 2 h. Finally, the agitation was reduced at 100 rpm and the dispersion was cooled down to room temperature.

TABLE 2 perfume oil composition

| Raw materials | wt % |
| --- | --- |
| Romascone ® a) | 20 |
| Verdox ® b) | 20 |
| Acétate de 4-(1,1-diméthyléthyl)-1-cyclohexyle c) | 20 |
| Cyclosal | 20 |
| Salicynile d) | 20 | a) Methyl 2,2-dimethyl-6-methylene-1-cyclohexanecarboxylate, origin: Firmenich SA, Geneva, Switzerland
b) 2-tert-butyl-1-cyclohexyl acetate, trademark from International Flavors & Fragrances, USA
c) origin: Firmenich SA, Geneva, Switzerland
d) (2Z)-2-phenyl-2-hexenenitrile, origin: Firmenich SA, Geneva, Switzerland

Example 3

Preparation of Comparative Microcapsules X

A solution of poly(vinyl alcohol) in water (45 g, 0.5 wt %, Mowiol 18-88, origin: Aldrich, Switzerland) was introduced in a beaker. A solution of perfume oil A (see table 1, 38 g) and polyisocyanate (0.27 g, Takenate® D-110N, Origin: Mitsui Chemicals, Japan) was introduced into the beaker. The reaction mixture was stirrer at 24,000 rpm with an Ultra Turrax for 2 min at room temperature (RT). A solution of guanidine carbonate (0.88 g, Origin: Aldrich, Switzerland) in water (4 g) was added dropwise with a syringe pump at room temperature over the course of 1 h. The resulting emulsion was warmed up to 70° C. over the course of 1 h. Temperature was maintained at 70° C. for 2 h and then cooled down to RT to afford a white dispersion (pH=9.7).

Example 4

Measurement of Microcapsule Zeta Potentials

The Zeta potential of microcapsules prepared according to examples 2 and 3 was measured with a Zetasizer Nano ZS (Malvern Instruments). This device was able to determine the Zeta potential for colloidal particles with a size ranging from 5 nm to 10 μm. Zeta potential measurements enabled to define the charge of the particle at its boundary with the surrounding solution. Within this boundary, the ions were strongly bound to the particle and they moved with it when an electrical field was applied, whereas the ions of the diffuse layer do not. Zeta potential of microcapsules of the present invention are listed in Table 3.

TABLE 3 zeta potential of microcapsules prepared with various copolymers 2-3

| Sample | Colloidal Stabilizer | Zeta Potential (mV) |
| --- | --- | --- |
| Microcapsules X* | PVOH 10-88 | −3 |
| A | PSI-5 | −91 |
| B | PSI-10 | −87 |
| C | PSI-20 | −81 |
| D | PSI-5-10 | −101 |
| G | PSI-10-10 | −102 |
| J | PSI-20-10 | −108 |
| H | PSI-10-20 | −110 |
| K | PSI-20-20 | −105 |
| F | PSI-5-30 | −69 |
| I | PSI-10-30 | −103 |
| L | PSI-20-30 | −105 |

The change of zeta potential indicates the presence of the polysuccinimide derivative in the shell. One can note that the microcapsules are highly negative.

One can see from FIG. 1 that the polysuccinimide derivative is located in the shell of the microcapsules thanks to the fluorescence of 1-pyrenemethylamine in the shell.

Example 5

Deposition Performance of Microcapsules According to the Invention

Procedure for Polymer Deposition on Cotton

The fabric process in a washing machine-was transferred to a laboratory scale. Microcapsules containing acridine as the fluorescent tracer were added to distilled water and diluted with demineralized cold pure water. Capsule dispersions (0.1 g) diluted in water (5 mL) were introduced in a beaker (1 L) and diluted with demineralized cold pure water (600 g). One cotton sheet (Eidgenssische Materialpreufanstalt (EMPA Switzerland), cotton test cloth Nr. 221, cut to ca. 12×12 cm2 sheets (average mass ca. 3.2 g) and pre-washed with an unperfumed detergent powder (classic powder detergent base (8-12% surfactants, 30-35% soda ash, 0-2% zeolite, 0-4% sodium silicate; 0-30% sodium chloride, 0-2% polymers, 5-8% moisture; sodium sulphate)) was added in the beaker and manually stirred for 3 min, left standing for 2 min, and then wrung out by hand and weighed (average mass ca. 7 g) to estimate the quantity of residual water. The fluorescence intensity was then measured from solutions of capsules before and after the addition of cotton sheet. The average spectra of ten scans were recorded between 470 and 500 nm, with an excitation wavelength of 240 nm, increment 1 nm, integration time 0.1 s, dark offset on, software correction for R detector, bandpass excitation 5 nm and bandpass emission 5 nm. All measurements were corrected using a blank solution (before and after cotton sheet stirring), which corresponded to microcapsules without acridine and with PVOH (0.4 g) as surfactant. Data were analyzed at 485 nm.

Figure 2:
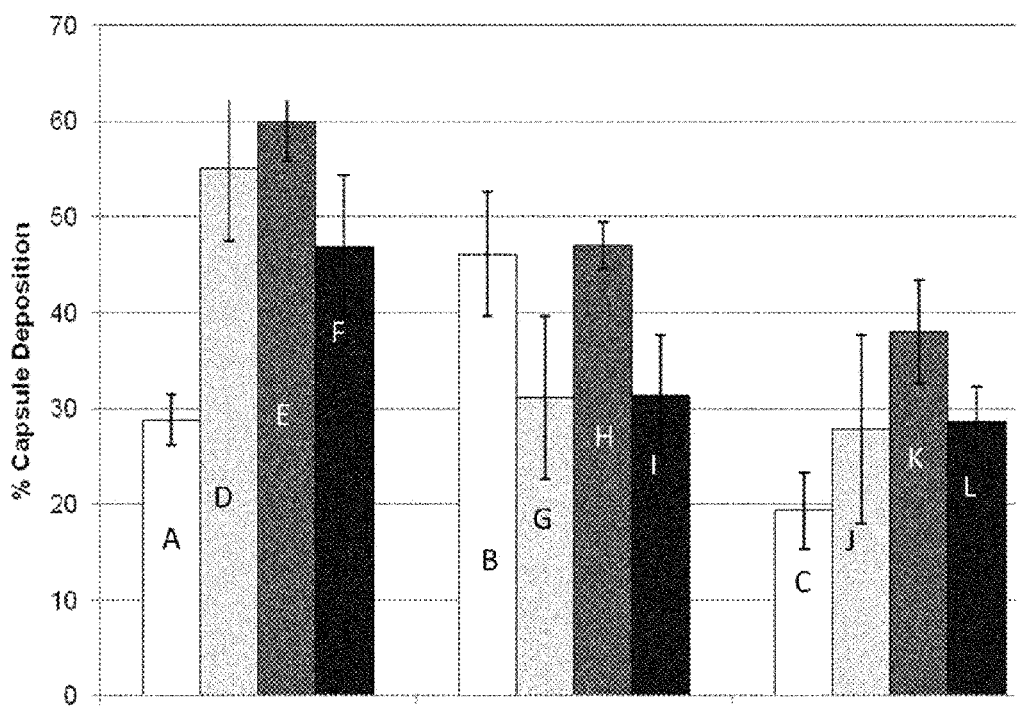
FIG. 2 represents the deposition performance of microcapsules according to the invention in a detergent powder.

FIG. 2 represents the data obtained for the deposition of the different microcapsules on fabric in water. One can conclude from these data that microcapsules according to the invention show good performance in terms of deposition. One can also conclude that best results are obtained for microcapsules containing polysuccinimide derivatives obtained by grafting DDA and dopamine on succinimide repeating units.

Example 6

Fabric Softener Application

Microcapsules A-L of the present invention are dispersed in a fabric softener base described in Table 4 to obtain a concentration of encapsulated perfume oil at 0.22%.

TABLE 4

Fabric softener composition

| Product | Origin | Wt % |
|---|---|---|
| Stepantex VL 90A | Stepan | 8.88 |
| Calcium Chloride Sol. 10% |  | 0.36 |
| Proxel GXL | Avecia | 0.04 |
| Water |  | 90.72 |
| TOTAL |  | 100 |

Example 7

Liquid Detergent Composition

Microcapsules A-L of the present invention are dispersed in a liquid detergent base described in Table 5 to obtain a concentration of encapsulated perfume oil at 0.22%.

TABLE 5

Liquid detergent composition

| Ingredients | Concentration [wt %] |
|---|---|
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Protease | 0.2 |
| Amylase | 0.2 |
| Mannanase | 0.2 |
| Acrylates/Steareth-20 Methacrylate structuring Crosspolymer[4] | 6 |
| Deionized Water | 27.4 |

[1] Hostapur SAS 60; Origin: Clariant
[2] Edenor K 12-18; Origin: Cognis
[3] Genapol LA 070; Origin: Clariant
[4] Aculyn 88; Origin: Dow Chemical

Example 8

Rinse-Off Conditioner

Microcapsules A-L of the present invention are dispersed in a rinse-off conditioner base described in table 6 to obtain a concentration of encapsulated perfume oil at 0.5%.

TABLE 6 rinse-off conditioner composition

| | Ingredients | Concentration [wt %] |
|---|---|---|
| A | Water deionized | 81.8 |
|  | Behentrimonium Chloride [1] | 2.5 |
|  | Hydroxyethylcellulose [2] | 1.5 |

TABLE 6-continued rinse-off conditioner composition

| | Ingredients | Concentration [wt %] |
|---|---|---|
| B | Cetearyl Alcohol [3] | 4 |
|  | Glyceryl Stearate (and) PEG-100 Stearate [4] | 2 |
|  | Behentrimonium Methosulfate (and) Cetyl alcohol (and) Butylene Glycol [5] | 4 |
|  | Ethoxy (20) Stearyl Alcohol [6] | 1 |
| C | Amodimethicone (and) Trideceth-12 (and) Cetrimonium Chloride [7] | 3 |
|  | Chlorhexidine Digluconate [8] 20% aqueous solution | 0.2 |
| D | Citric acid 10% aqueous sol. till pH 3.5-4 | q.s. |
|  | TOTAL: | 100 |

[1] Genamin KDM P, Clariant
[2] Tylose H10 Y G4, Shin Etsu
[3] Lanette O, BASF
[4] Arlacel 165-FP-MBAL-PA-(RB), Croda
[5] Incroquat Behenyl TMS-50-MBAL-PA-(MH) HA4112, Croda
[6] SP Brij S20 MBAL-PA(RB), Croda
[7] Xiameter DC MEM-0949 Emulsion, Dow Corning
[8] Alfa Aesar

Example 9

Shampoo Composition

Microcapsules A-L of the present invention are weighed and mixed in a shampoo composition to add the equivalent of 0.2% perfume.

TABLE 7

Shampoo composition

| | Ingredients | Concentration [wt %] |
|---|---|---|
| A | Water deionized | 44.4 |
|  | Polyquaternium-10 [1] | 0.3 |
|  | Glycerin 85% [2] | 1 |
|  | DMDM Hydantoin [3] | 0.2 |
| B | Sodium Laureth Sulfate [4] | 28 |
|  | Cocamidopropyl Betaine [5] | 3.2 |
|  | Disodium Cocoamphodiacetate [6] | 4 |
|  | Ethoxy (20) Stearyl Alcohol [6] | 1 |
| C | Sodium Laureth Sulfate [4] | 3 |
|  | Glyceryl Laureate [7] | 0.2 |
| D | Water deionized | 1 |
|  | Sodium Methylparaben [8] | 0.1 |
| E | Sodium Chloride 10% aqueous sol. | 15 |
|  | Citric acid 10% aqueous sol. till pH 5.5-6 | q.s. |
|  | Perfume | 0.5 |
|  | TOTAL: | 100 |

[1] Ucare Polymer JR-400, Noveon
[2] Schweizerhall
[3] Glydant, Lonza
[4] Texapon NSO IS, Cognis
[5] Tego Betain L 50, Evonik
[6] Amphotensid GB 2009, Zschimmer & Schwarz
[7] Monomuls 90 L-12, Gruenau
[8] Nipagin Monosodium, NIPA

Example 10

Antiperspirant Roll-on Emulsion Composition

Microcapsules A-L of the present invention are weighed and mixed in antiperspirant roll-on emulsion composition to add the equivalent of 0.2% perfume.

TABLE 8

Antiperspirant roll-on emulsion composition

| Ingredient | Amount (wt %) |
| --- | --- |
| Steareth-2[1)] (Part A) | 3.25 |
| Steareth-21[2)] (Part A) | 0.75 |
| PPG-15 Stearyl Ether[3)] (Part A) | 4 |
| WATER deionised (Part B) | 51 |
| Aluminum Chlorohydrate 50% aqueous solution[4)] (Part C) | 40 |
| Fragrance (Part D) | 1 |

[1)] BRIJ 72; origin: ICI
[2)] BRIJ 721; origin: ICI
[3)] ARLAMOL E; origin: UNIQEMA-CRODA
[4)] LOCRON L; origin: CLARIAN Part A and B are heated separately to 75° C.; Part A is added to Part B under stirring and the mixture is homogenized for 10 min. Then, the mixture is cooled under stirring; and Part C is slowly added when the mixture reached 45° C. and Part D when the mixture reached at 35° C. while stirring. Then the mixture is cooled to room temperature.

Example 11

Shower-Gel Composition

Microcapsules A-L of the present invention are weighed and mixed in the following composition to add the equivalent of 0.2% perfume.

TABLE 9

Shower gel composition

| Ingredients | Amount (% wt) | Function |
| --- | --- | --- |
| WATER deionised | 49.350 | Solvent |
| Tetrasodium EDTA [1)] | 0.050 | Chelating agent |
| Acrylates Copolymer[2)] | 6.000 | Thickener |
| Sodium C12-C15 Pareth Sulfate [3)] | 35.000 | Surfactant |
| Sodium Hydroxide 20% aqueous solution | 1.000 | pH adjuster |
| Cocamidopropyl Betaine[4)] | 8.000 | Surfactant |
| Methylchloroisothiazolinone and Methylisothiazolinone[5)] | 0.100 | Preservative |
| Citric Acid (40%) | 0.500 | pH adjuster |

[1)] EDETA B POWDER; trademark and origin: BASF
[2)] CARBOPOL AQUA SF-1 POLYMER; trademark and origin: NOVEON
[3)] ZETESOL AO 328 U; trademark and origin: ZSCHIMMER & SCHWARZ
[4)] TEGO-BETAIN F 50; trademark and origin: GOLDSCHMIDT
[5)] KATHON CG; trademark and origin: ROHM & HASS

The invention claimed is:

1. A core-shell microcapsule comprising:
an oil based core comprising a hydrophobic material, wherein the hydrophobic material comprises a perfume, and
a shell formed from the reaction between a polyfunctional monomer and a polysuccinimide derivative, wherein the polysuccinimide derivative is obtained by grafting at least one amine to at least one succinimide repeating unit;
wherein the amine is selected from the group consisting of 1-Dodecylamine (DDA), 1-decylamine, dopamine, 2-aminoethan-1-ol, 3-amino-propan-1-ol, 6-amino-hexan-1-ol, and mixtures thereof;
wherein the polysuccinimide derivative is selected from the group consisting of polysuccinimide-co-poly(n-ethylaspartamide), polysuccinimide-co-poly(n-butylaspartamide), polysuccinimide-co-poly(n-hexylaspartamide), polysuccinimide-co-poly(n-dodecylaspartamide), polysuccinimide-co-poly(n-dodecylaspartamide)-co-poly(3,4-dihydroxybenzylaspartamide), and mixtures thereof; and
wherein the polyfunctional monomer is selected from the group consisting of at least one polyisocyanate, polyanhydride, poly acyl chloride, polyepoxide, acrylate monomers, polyalkoxysilane, and mixtures thereof.

2. The microcapsule according to claim 1, wherein the zeta potential of said microcapsule is comprised between 50 mV and −120 mV.

3. A perfuming composition comprising:
(i) a plurality of the microcapsules according to claim 1,
(ii) at least one ingredient selected from the group consisting of a perfumery carrier and a perfumery base, and
(iii) optionally at least one perfumery adjuvant.

4. A consumer product comprising:
a personal care active base, and
a plurality of the microcapsules according to claim 1,
wherein the consumer product is in the form of a personal care composition.

5. A consumer product comprising:
a home care or a fabric care active base, and
a plurality of the microcapsules according to claim 1,
wherein the consumer product is in the form of a home care or a fabric care composition.

6. The microcapsule according to claim 1, wherein the polyfunctional monomer is at least one polyisocyanate having at least two isocyanate groups.

7. A process for the preparation of a core-shell microcapsule slurry, the method comprising the following steps:
a) dissolving at least one polyfunctional monomer, in a hydrophobic material to form an oil phase;
b) dispersing the oil phase obtained in step a) into an aqueous solution comprising a polysuccinimide derivative to form an oil-in-water emulsion; and
c) performing a curing step to form core-shell microcapsules in the form of a slurry;
wherein the hydrophobic material comprises a perfume;
wherein the shell is formed from the reaction between the polyfunctional monomer and the polysuccinimide derivative, wherein the polysuccinimide derivative is obtained by grafting at least one amine to at least one succinimide repeating unit;
wherein the amine is selected from the group consisting of 1-Dodecylamine (DDA), 1-decylamine, dopamine, 2-aminoethan-1-ol, 3-amino-propan-1-ol, 6-amino-hexan-1-ol, and mixtures thereof;
wherein the polysuccinimide derivative is selected from the group consisting of polysuccinimide-co-poly(n-ethylaspartamide), polysuccinimide-co-poly(n-butylaspartamide), polysuccinimide-co-poly(n-hexylaspartamide), polysuccinimide-co-poly(n-dodecylaspartamide), polysuccinimide-co-poly(n-dodecylaspartamide)-co-poly(3,4-dihydroxybenzylaspartamide), and mixtures thereof; and
wherein the polyfunctional monomer is selected from the group consisting of at least one polyisocyanate, polyanhydride, poly acyl chloride, polyepoxide, acrylate monomers, polyalkoxysilane, and mixtures thereof.

8. The process according to claim 7, wherein the polysuccinimide derivative is used in an amount comprised between 0.1% and 5% by weight, relative to the total weight of the emulsion obtained in step b).

9. The process according to claim 7, wherein the at least one polyfunctional monomer is used in an amount of between 0.5% and 10% by weight, relative to the total weight of the oil phase.

10. The process according to claim 7, wherein the at least one polyfunctional monomer is used in an amount of between 2% and 3% by weight, relative to the total weight of the oil phase.

11. The process according to claim 1, wherein the at least one polyfunctional monomer is at least one polyisocyanate having at least two isocyanate groups.

12. The process according to claim 7, wherein the aqueous phase comprises a reactant selected from the group consisting of a polyamine, a polyol, and a mixture thereof.

\* \* \* \* \*